US007435212B2

(12) United States Patent
Chen

(10) Patent No.: US 7,435,212 B2
(45) Date of Patent: Oct. 14, 2008

(54) ARTIFICIAL INSEMINATION DEVICE WITH AN INNER CATHETER FOR ANIMALS

(76) Inventor: Sheng-Jui Chen, No. 14, Lane 291, Shin-Te St., Pyng-Jenn City, Taoyuan (TW)

( * ) Notice: Subject to any disclaimer, the term of this patent is extended or adjusted under 35 U.S.C. 154(b) by 442 days.

(21) Appl. No.: 11/208,750

(22) Filed: Aug. 23, 2005

(65) Prior Publication Data

US 2007/0055094 A1 Mar. 8, 2007

(51) Int. Cl.
*A61D 7/00* (2006.01)
*A61B 17/43* (2006.01)

(52) U.S. Cl. .................................................... 600/35

(58) Field of Classification Search ............. 600/33-35; 119/14.21, 174; 604/510, 515, 906
See application file for complete search history.

(56) References Cited

U.S. PATENT DOCUMENTS 6,527,703 B2 * 3/2003 Simmet ....................... 600/33
6,726,619 B2 * 4/2004 Gil Pascual .................. 600/35
6,860,235 B2 * 3/2005 Anderson et al. ........... 119/174
7,175,590 B2 * 2/2007 Christine et al. .............. 600/35

* cited by examiner

*Primary Examiner*—John P Lacyk
(74) *Attorney, Agent, or Firm*—Rosenberg, Klein & Lee

(57) ABSTRACT

An improved artificial insemination device with an inner catheter for animals is disclosed. The device is characterized by having a thin flexible tube and a positioning stop member installed respectively at the front end and rear end of an inner catheter that is movably inserted in the catheter tube. The thin flexible tube instantly extends forward from the front end of inner catheter when semen is squeezed into the inner catheter. Thus after the nozzle of catheter tube reaches the first cervical ring of the animal, the inner catheter only needs to extend inward a proper distance, and the semen, with the aid of squeeze force and the thin flexible tube advancing freely along the cervical tract, could be delivered to uterus smoothly, swiftly and accurately without causing trauma to the uterus. Also with the arrangement of the positioning stop member, the distance the inner catheter travels inward can be set. As the depth and location of inward extension are under proper control, the practice of artificial insemination is made simple, convenient, fast, efficient and safe for the animal.

5 Claims, 17 Drawing Sheets

ARTIFICIAL INSEMINATION DEVICE WITH AN INNER CATHETER FOR ANIMALS

BACKGROUND OF THE INVENTION

1) Field of the Invention

The present invention relates to an improved artificial insemination device with an inner catheter for animals, more particularly, a simple, practical, ideal and inventive device that is easy and convenient to use and allows animal semen to reach the two ducts to uterine horns or the uterus swiftly and smoothly, thereby improving the success rate of artificial insemination and effectively saving the amount of semen needed. The invention herein requires minimal amounts of insemination semen and offers economic benefit. It also renders artificial insemination safer, more hygienic, and more humane.

2) Description of the Prior Art

The assembly and operation of conventional artificial insemination device for animals as shown in FIG. 1 and FIG. 2, typically comprises a plastic catheter tube 10 of certain hardness and a nozzle 20 made of softer material installed protrusively on the front end of catheter tube 10. When artificial insemination is carried out, the catheter tube 10 and nozzle 20 are inserted along the vagina 11 of female animal body 1 until the nozzle 20 at the front penetrates into cervical tract 12. Subsequently, the insertion tube 31 of the semen dispenser (bag or syringe) 30 containing the animal semen is inserted into the rear end of catheter tube 10, and as the operator continuously squeezes the semen dispenser (bag or syringe) 30, the semen contained therein is ejected into the cervical tract 12 through the nozzle 20 of catheter tube 10, where the uterus 13 contracts to draw in semen from cervical tract 12. Although the configuration and operation of such artificial insemination device achieve the purpose of artificial insemination in animals effectively, there are some drawbacks:

1. After the catheter tube 10 penetrates the vagina 11 of female animal body 1, the nozzle 20 at the front is pushed approximately to the position of first cervical ring 121 of cervical tract 12, but there remains considerable distance between the first cervical ring 121 and the uterus. Although the contraction of uterus 13 could draw in the semen from cervical tract 12, a large amount of semen ejected from the nozzle 20 initially accumulates at the position of first cervical ring 121 and cannot instantly flow into the uterus 13. What happens most frequently is that the semen accumulated at the first cervical ring 121 often backflows outside the vaginal orifice 111. As such, not only semen is wasted, the amount of semen that flows into the uterus 13 is proportionately lessened, hence decreasing the probability of successful insemination.

2. In response to the problem of semen backflow, operators commonly dilute the semen fluid many folds (typically 5 cc is diluted into 50-120 cc) and enlarge the inner diameter of catheter tube to accommodate and provide more semen fluid for insemination. But the massive dilution of semen fluid apparently reduces the rate of fertilization and the number of fetus, while using more semen incurs waste directly.

3. As described above, the semen in catheter tube 10 is directly released from the nozzle 20, and when nozzle 20 penetrates the cervical tract 12 from outside the female animal body 1, the accidental admittance of contaminants from outside the body or the vagina 11 is difficult to avoid as the semen flows into the uterus 13. As such, the risk of bacteria infection and inflammation of the vagina, cervical tract, and even the uterus of the animal during artificial insemination is high and, at the same time, the safety of fetus carried in the uterus 13 is jeopardized.

4. To improve the success rate and safety of artificial insemination, the operation of artificial insemination requires professional personnel (such as veterinarians or specialized technical personnel) and, as such, to big animal farms (such as pig farmers), it incurs heavy economic burden and demands considerable professional manpower.

5. After the operator utilizes the catheter tube 10 and nozzle 20 to penetrate the vagina 11 and cervical tract 12 of female animal body 1, he has to use one hand to hold the rear end of catheter tube 10 and the other hand to grip and squeeze the semen dispenser 30, which is apparently more troublesome, inconvenient, cumbersome, and time consuming in operation.

To render animal artificial insemination process more efficient and humane, some operators would use accessory devices. As shown in FIG. 3, such devices include an AI Buddy 40, an elastic saddle-like apparatus resembling the two front legs of an animal, wherein a connector 50 with open posterior is installed at the rear end of catheter tube 10, with a positioning strap 41 disposed between the AI Buddy 40 and the connector 50; as such, during the artificial insemination procedure, the operator straddles the AI Buddy 40 over the back of the female animal 1 such that the female animal feels that a male animal has mounted with its two front legs, a guide bush 60 is then placed at the vaginal orifice 111 of female animal body 1 and after the catheter tube 10 and nozzle 20 penetrate the vagina 11 and reaches the cervical tract 12 through the guide bush 60, the rear end of catheter tube 10 is flexed upward and directly secured by the positioning strap 41 connected to the AI Buddy 40; following the ingress of a semen dispenser 30 insertion tube 31 into the connector 50, the operator only has to squeeze the semen dispenser 30. In such approaches, the operator needs to use both hands at the same time, one for grasping the catheter tube 10 and one for squeezing the semen dispenser 30, a procedure that is troublesome and time consuming, but nevertheless an effective improvement. However, existent shortcomings that have not been improved include semen backflow that wastes semen, which is uneconomical and lowers insemination success rate; the easy inflow of contaminants from the outside of the female animal body into the vagina, cervical tract, and uterus that endanger the health of the female animal and fetus carried in the uterus; and the requiring of specialized personnel for operation, which is uneconomical and involves additional manpower.

To increase the success rate of artificial insemination, an improved artificial insemination device for animals as shown in FIG. 4 and FIG. 5 (U.S. Pat. No. 6,526,917) has been disclosed, wherein the front end opening 421 of catheter tube 420 is inserted into a sheath-like membrane 410 and the leading edge 412 of membrane 410 is snapped into a positioning ring 422 of catheter tube 420. Subsequently, nozzle 440 is inserted into the front end of catheter tube 420 to immobilize membrane 410. After nozzle 440 is inserted into the front end of catheter tube 420, the various components including the member 410 sandwiched between nozzle 440 and catheter tube 420 can be further secured to each other by sonically welded or heat staked. The object of such artificial insemination assembly is to cause the tip 411 of sheath-like membrane 410 to begin unfolding in an inside-out manner not unlike removing one's sock by pulling from the open end when semen is squeezed into the rear end of catheter tube 420 and enters the uterus along the cervical tract where semen is ejected from the opening of tip 411 to enhance the efficiency of insemination, prevent the entry of contaminants into uterus, and prevent the backflow of semen. Such artificial insemination apparatus is more effective in comparison with prior art. But it still has some drawbacks in actual implementation:

1. Given that membrane 410 is inserted from the front end opening 421 of catheter tube 420 and secured to nozzle 440 via a leading edge 412, the tip 411 of membrane, when squeezed inside-out under the pressure of semen, must travel through the pathway B (FIG. 4) of nozzle 440 before entering the cervical tract of animal. Thus in order for membrane 410 to enter the uterus of animal, it must have certain length. As we know, the longer the membrane, greater squeeze force to expose it outside the nozzle is required, rendering the whole operation more troublesome. In particular when the semen dispenser is in bag shape, the force generated from squeeze is not as much as that of bottle or syringe, which construes a limitation in implementation.

2. Given that the leading edge 412 of membrane 410 is snapped into the positioning ring 422 of catheter tube 420, membrane 410 is tightly attached to the periphery of tube 420 under certain tension, and subsequently nozzle 440 is tightly conjoined to the periphery of membrane 410. What happens most frequently is that when the membrane 410 under tension is pushed by the exertion of nozzle 440, perforation tends to occur around the edge of front end of catheter tube 420 (shown as C in FIG. 4). In such event, when semen is squeezed into catheter tube 420, the perforation would cause air leakage, which keeps membrane 410 from being squeezed out quickly and smoothly, thereby resulting in poor execution or even the failure of artificial insemination.

3. Given that membrane 410 is inserted into catheter tube 420 from its opening 421, the inner diameter of catheter tube 420 (i.e. the hollow space 424) must be bigger. But bigger tube directly increases the consumption of semen, the same as in prior art. Such apparatus apparently does not offer the economic benefit of saving the usage of semen.

4. To prevent trauma to the animal during artificial insemination, the nozzle is usually made of elastomeric material. If the force used is improper or the animal does not stay still during artificial insemination, the front part of nozzle is prone to deformation or bend which might block the semen pathway. Under the circumstances, it is likely that the membrane 410 disposed inside catheter tube 420 will not extend under pressure to achieve artificial insemination.

5. As described above, membrane 410 must have certain length and is directly inserted in larger diameter in catheter tube 420. When the force from the squeeze of semen pushes membrane 410 out of nozzle 440 and into the cervical tract of animal, the long and large-sized membrane will encounter greater resistance inside the narrow and winding cervical tract and become more difficult to extend. More so, if the squeeze force is smaller, it is likely that the tip of membrane 411 will not reach uterus, rendering artificial insemination an unstable and uncertain operation.

FIG. 6 and FIG. 7 depict another artificial insemination apparatus for animals, characterized in which a longer plastic inner catheter 70 is movably inserted in the catheter tube 10 of a conventional device that comes with a nozzle 20, and a smaller second nozzle 80 is disposed at the forward portion of inner catheter 70. The object of such artificial insemination assembly is to allow the operator to advance the smaller inner catheter 70 inside the catheter tube 10 more smoothly along the cervical tract and bring the smaller second nozzle 80 to the location of uterus after the catheter tube 10 and nozzle 20 enter the cervical tract of female animal body and the nozzle 20 reaches the first cervical ring. Subsequently, semen contained in the semen dispenser (bag or syringe) is expelled from the rear end of inner catheter and enters uterus smoothly via the second nozzle 80. Undeniably, such design facilitates the delivery of semen to the uterus and the use of smaller inner catheter 70 saves the volume of semen required. Still operators find some deficiencies with the device after using it in actual operations. That is, when the inner catheter is extended inward, operator is unable to see if the second nozzle 80 at the front has reached the uterus and can only rely on experience to control the depth of inward extension. What happens most frequently in actual implementation is that the inner catheter 70 overextends and injures the uterus. In the attempt to prevent injury to uterus, some operators shortened the extension depth of inner catheter 70, which however defeats the original purpose of disposing such a tube and results in backflow of semen. Also, as the animal does not stay still during artificial insemination, a free-moving inner catheter 70 is prone to displacement during the procedure and causes trauma to the uterus.

SUMMARY OF THE INVENTION

The primary object of the present invention is to provide an improved artificial insemination device with an inner catheter for animals, characterized in which a thin flexible tube is disposed inside the front end of inner catheter, which extends automatically forward and outward when semen is squeezed into the inner catheter. As such, after the ingress of catheter tube and nozzle into the cervical tract of animal and the positioning of nozzle at the first cervical ring, the inner catheter only needs to conveniently advance a certain distance for the semen, with the aid of squeeze force and the thin flexible tube advancing freely along the cervical tract, to be delivered to the uterus smoothly, swiftly and accurately. It not only enhances the efficiency of artificial insemination but also renders the whole procedure safer for the female animal.

Another object of the present invention is to provide an improved artificial insemination device with an inner catheter for animals, characterized in which a positioning stop member is disposed at the rear end of inner catheter to control the distance of its inward extension. As such, the advancing of the inner catheter and a second nozzle inside the cervical tract of animal is made simpler, more convenient, faster, and more efficient. Similarly the inward extension step becomes more stable in terms of depth and location without the concern of traumatizing the uterus of animal during the procedure.

A further object of the present invention is to provide an improved artificial insemination device with an inner catheter for animals, wherein by conveniently advancing the inner catheter inside the cervical tract a proper distance after engaging the nozzle of catheter tube at the first cervical ring, the length of thin flexible tube inside the front end of inner catheter can be effectively shortened. As such, the pressure required from squeezing the semen dispenser to push the thin flexible tube forward and outward is also reduced, which facilitates the movement of thin flexible tube in the cervical tract and renders the whole process simpler, thereby improving the efficiency of artificial insemination.

Yet another object of the present invention is to provide an improved artificial insemination device with an inner catheter for animals, wherein by setting the length of said inner catheter to allow it and the thin flexible tube at its front to conveniently and smoothly advance inside the cervical tract of animal without resistance, semen can be swiftly and accurately delivered to uterus. As such, semen used for artificial insemination does not require massive dilution, while only more concentrated semen in small amount needs to be injected into the inner catheter. Thus the present invention not only offers the economic benefit of saving the semen used, the fertilization rate and the number of fetus are also expected to increase.

Yet another object of the present invention is to provide an improved artificial insemination device with an inner catheter for animals, wherein the second nozzle disposed at the front end of inner catheter is an assembly of two rubber sheaths having proper rigidity and elasticity that will not bend or deform after it enters the cervical tract, and the thin flexible tube immobilized therein is not prone to perforation. As such, the forward and outward extension movement of the thin flexible tube is made smoother and more accurate, rendering the practice of artificial insemination more efficient.

The objects, features and effects of the invention are described in details below with accompanying drawing and embodiments.

DETAILED DESCRIPTION OF THE INVENTION

Figure 1:
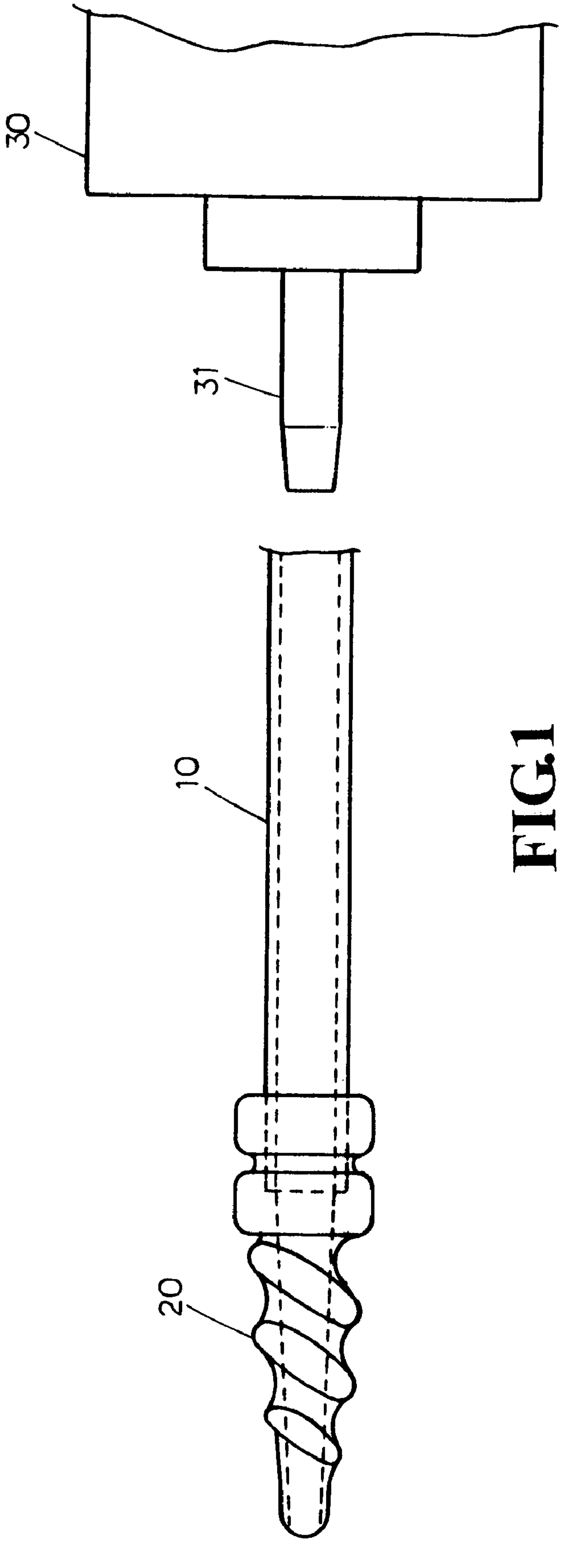
FIG.1 PRIOR ART
FIG. 1 is a schematic of a conventional artificial insemination device with a semen dispenser.
Figure 2:
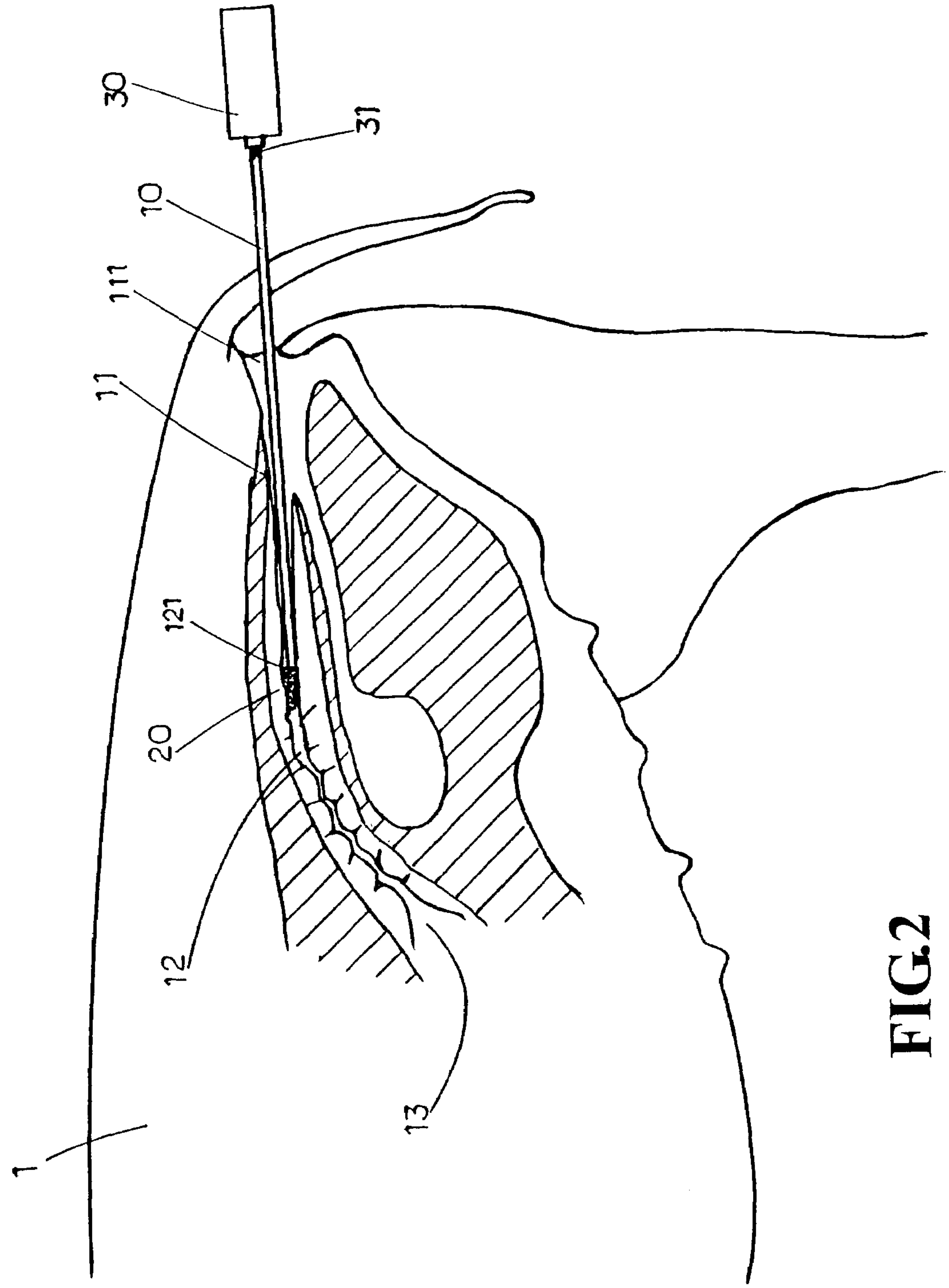
FIG.2 PRIOR ART
FIG. 2 is a schematic of the artificial insemination device in FIG. 1 penetrating the body of a female animal.
Figure 3:
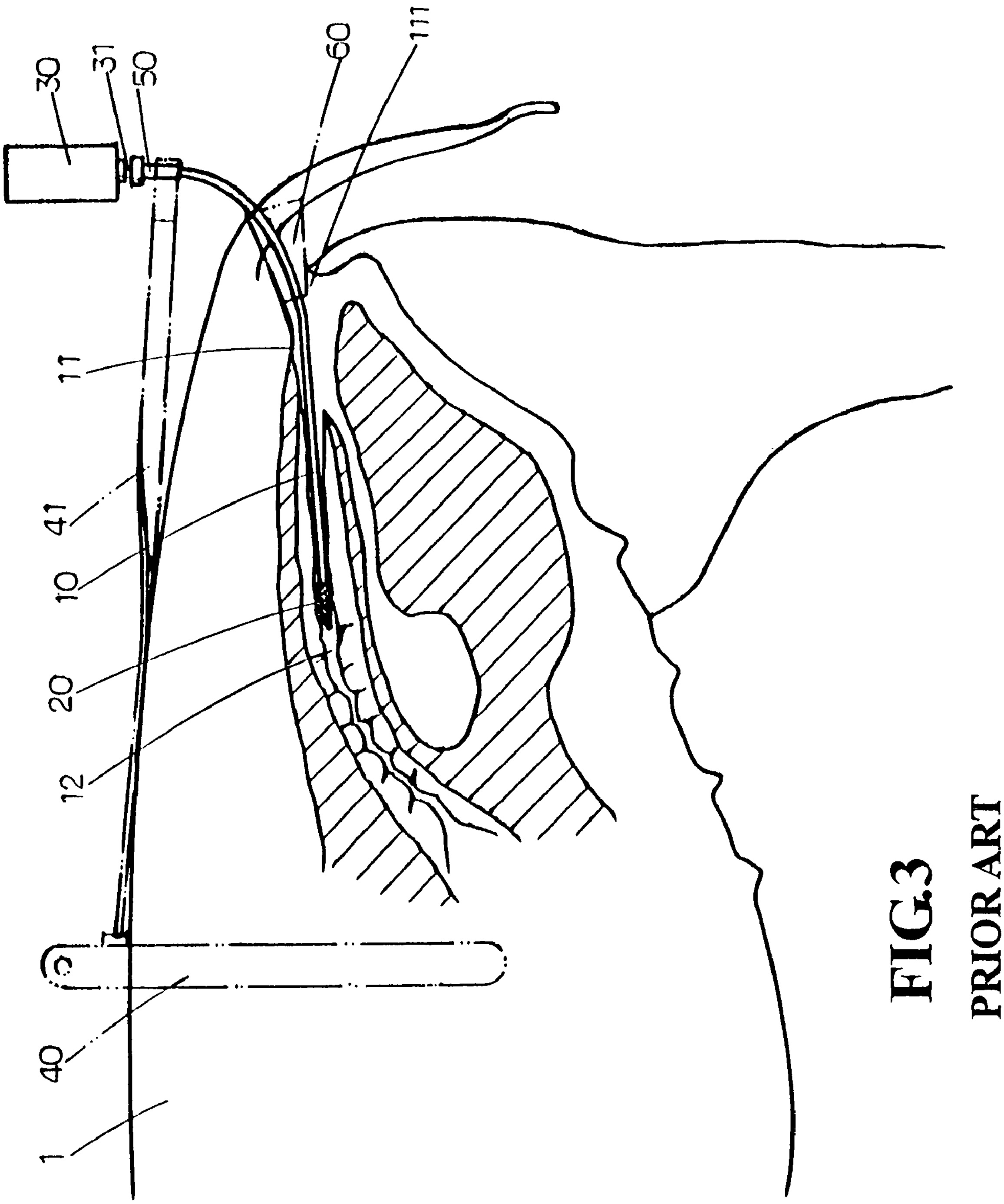
FIG.3 PRIOR ART
FIG. 3 is a schematic of a conventional artificial insemination device, equipped with a connector and an AI Buddy, penetrating the body of a female animal.
Figure 4A:
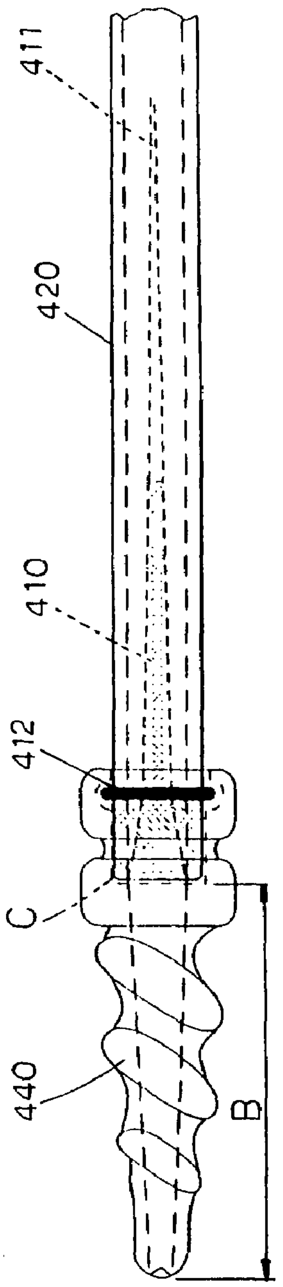
FIG.4A PRIOR ART
FIGS. 4A and 4B are schematic views of the before and after deployment, respectively, of the catheter in accordance with the artificial insemination device disclosed in U.S. Pat. No. 6,526,917.
Figure 4B:
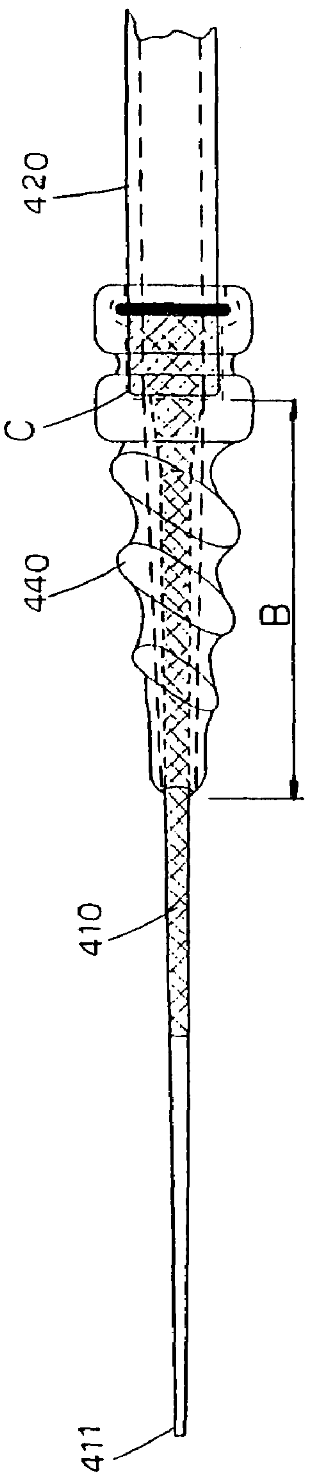
FIG.4B PRIOR ART
Figures 5A, 5B, 5C:
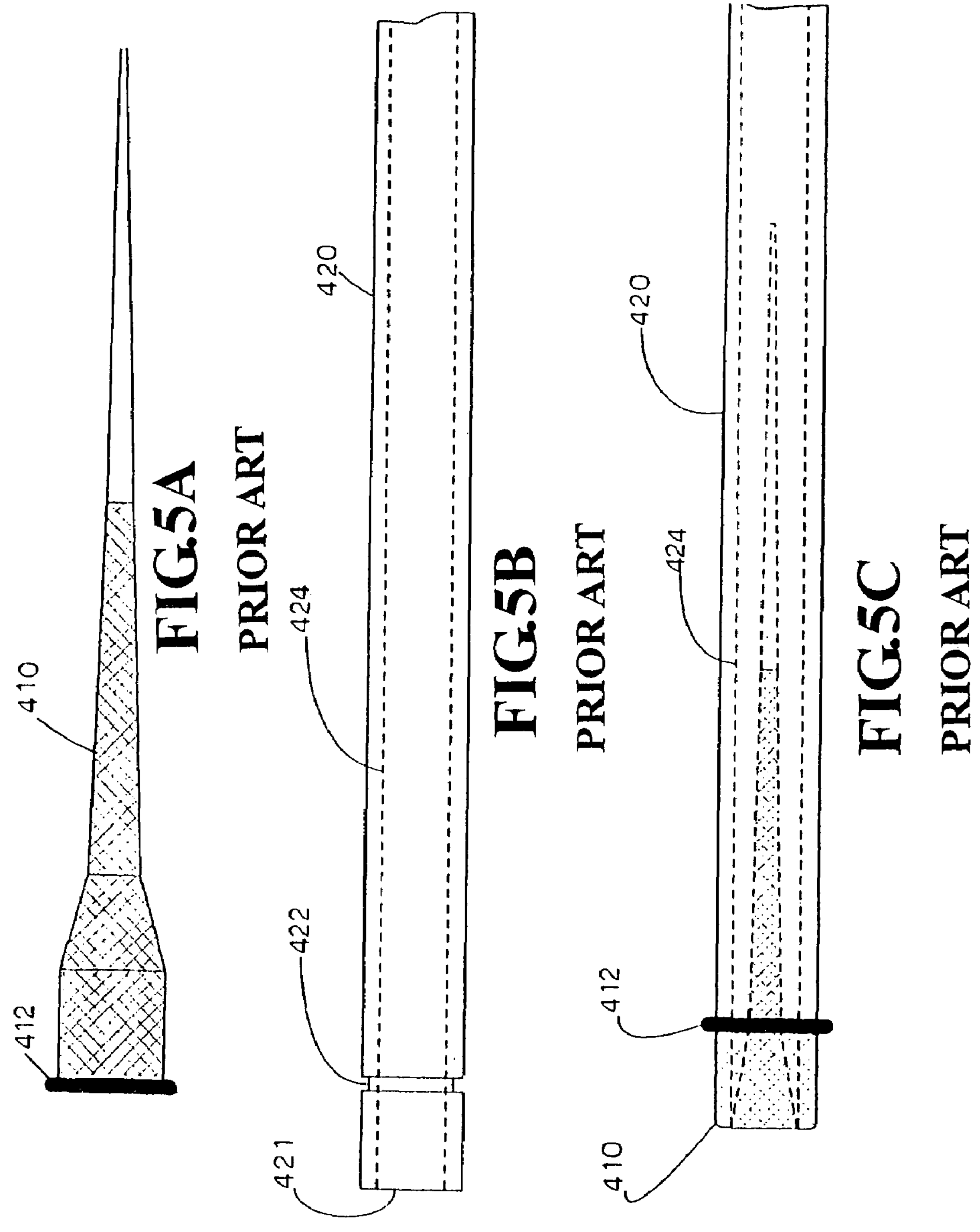
FIG.5A PRIOR ART
FIG.5B PRIOR ART
FIG.5C PRIOR ART
FIGS. 5A and 5F show the assembly of the catheter of FIGS. 4A and 4B.
Figures 5D, 5E, 5F:
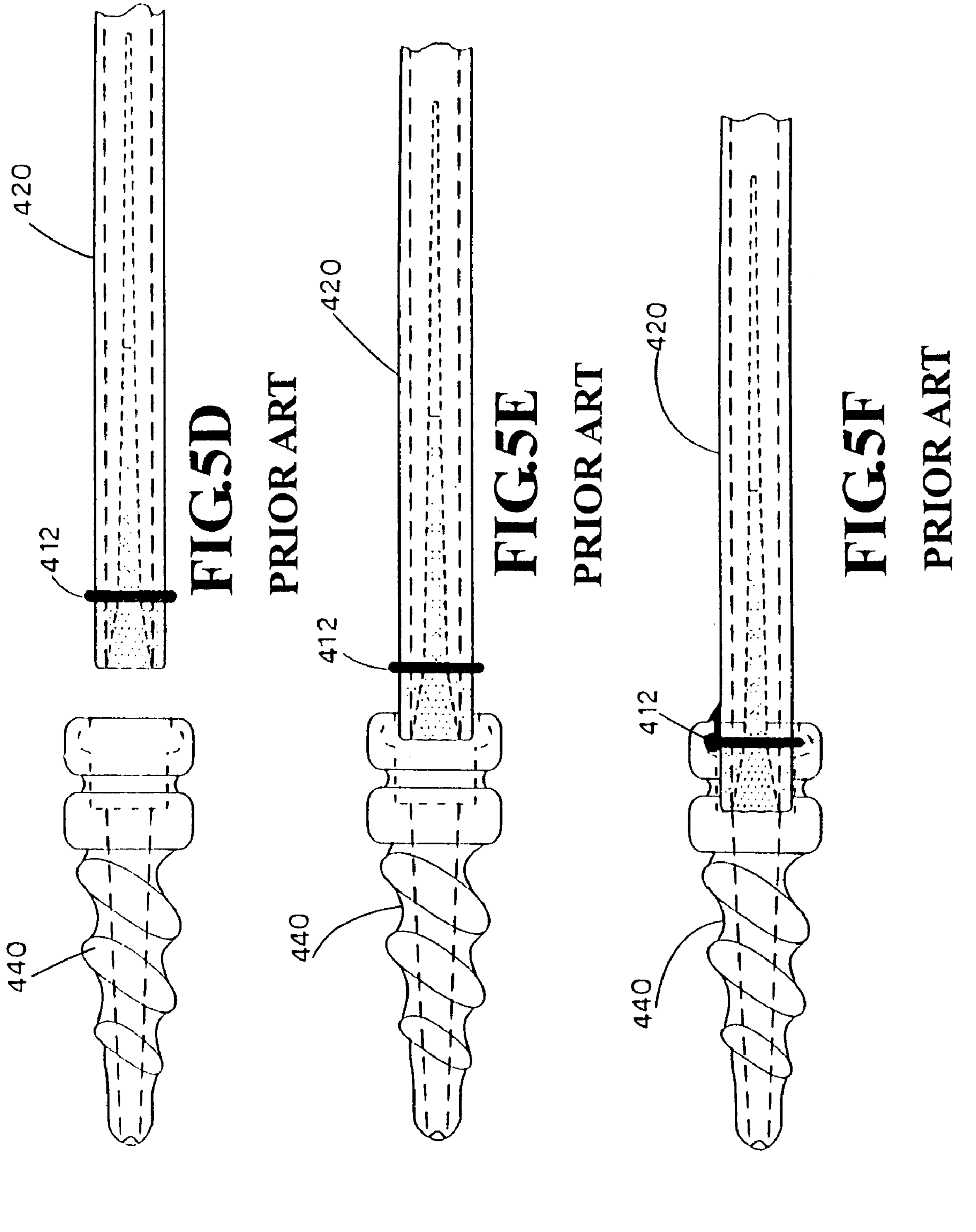
FIG.5D PRIOR ART
FIG.5E PRIOR ART
FIG.5F PRIOR ART
Figure 6:
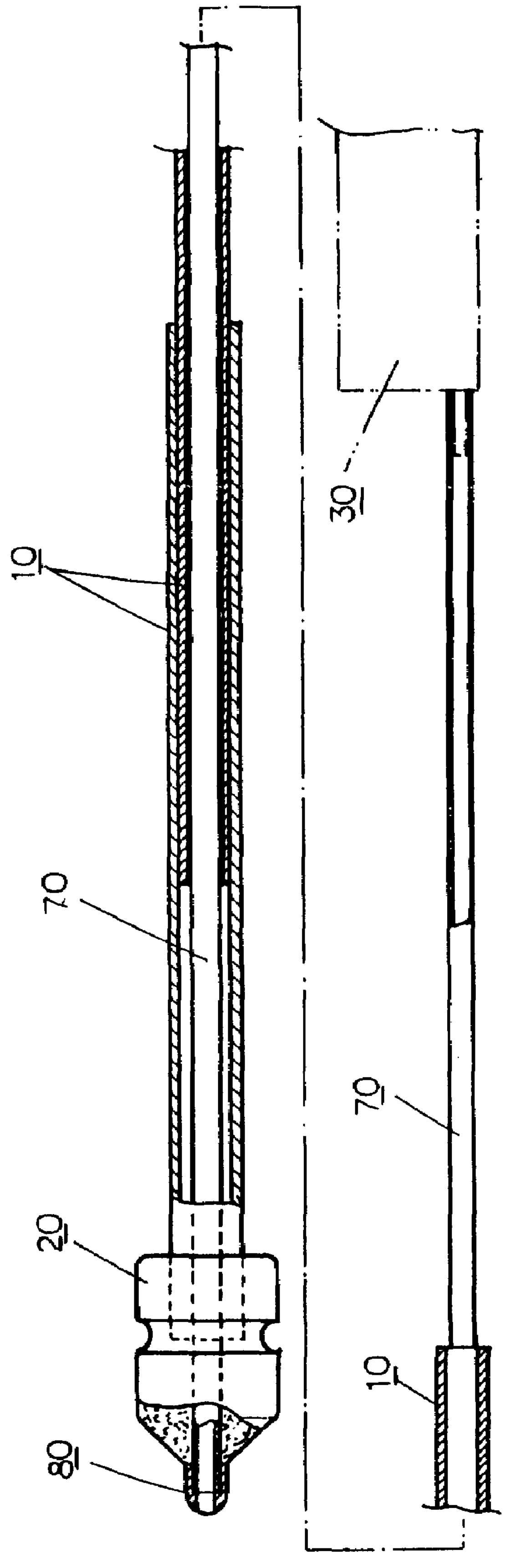
FIG.6 PRIOR ART
FIG. 6 shows the diagrams of the inner catheter and second nozzle of another prior art in retracted state.
Figure 7:
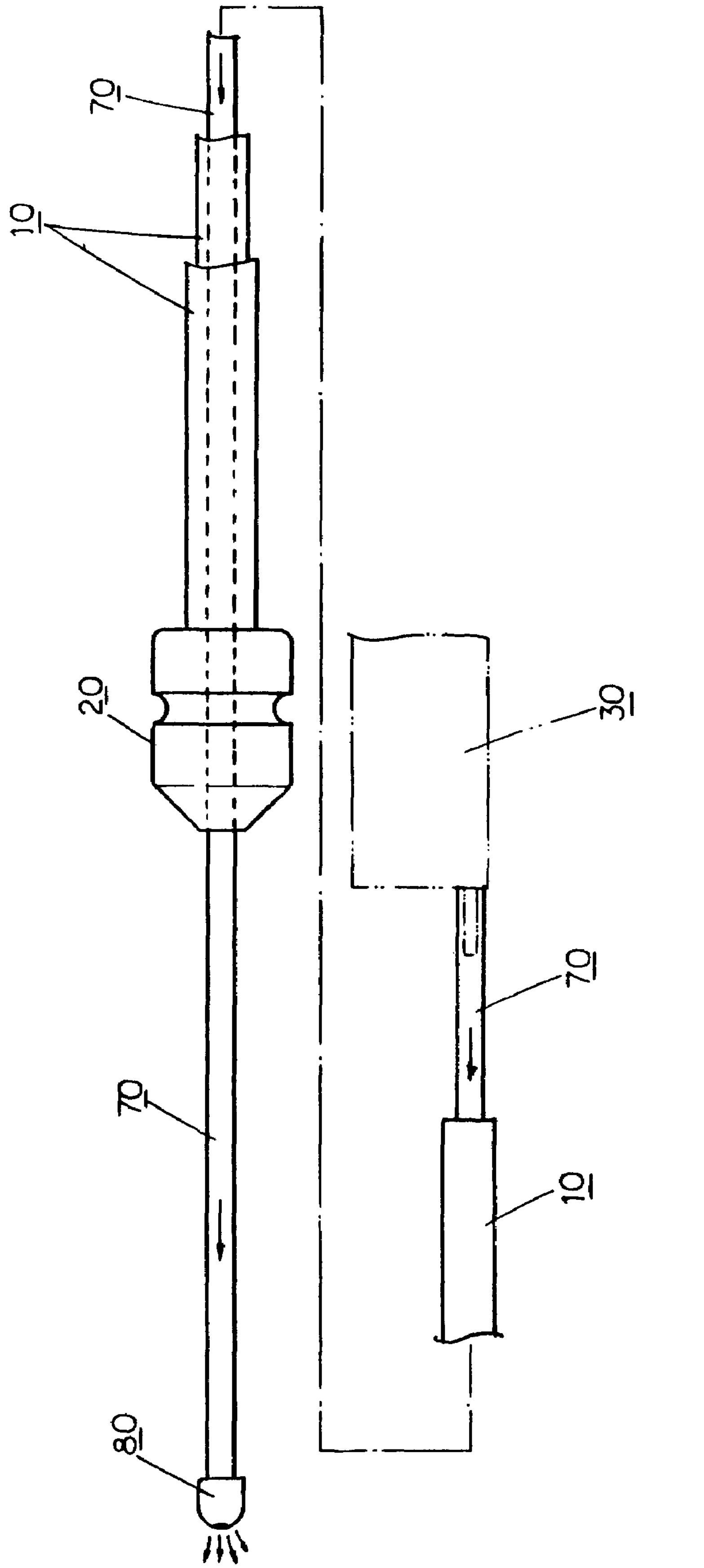
FIG.7 PRIOR ART
FIG. 7 shows the diagrams of the inner catheter and second nozzle of another prior art in FIG. 6 in the state of forward extension.
Figure 8:
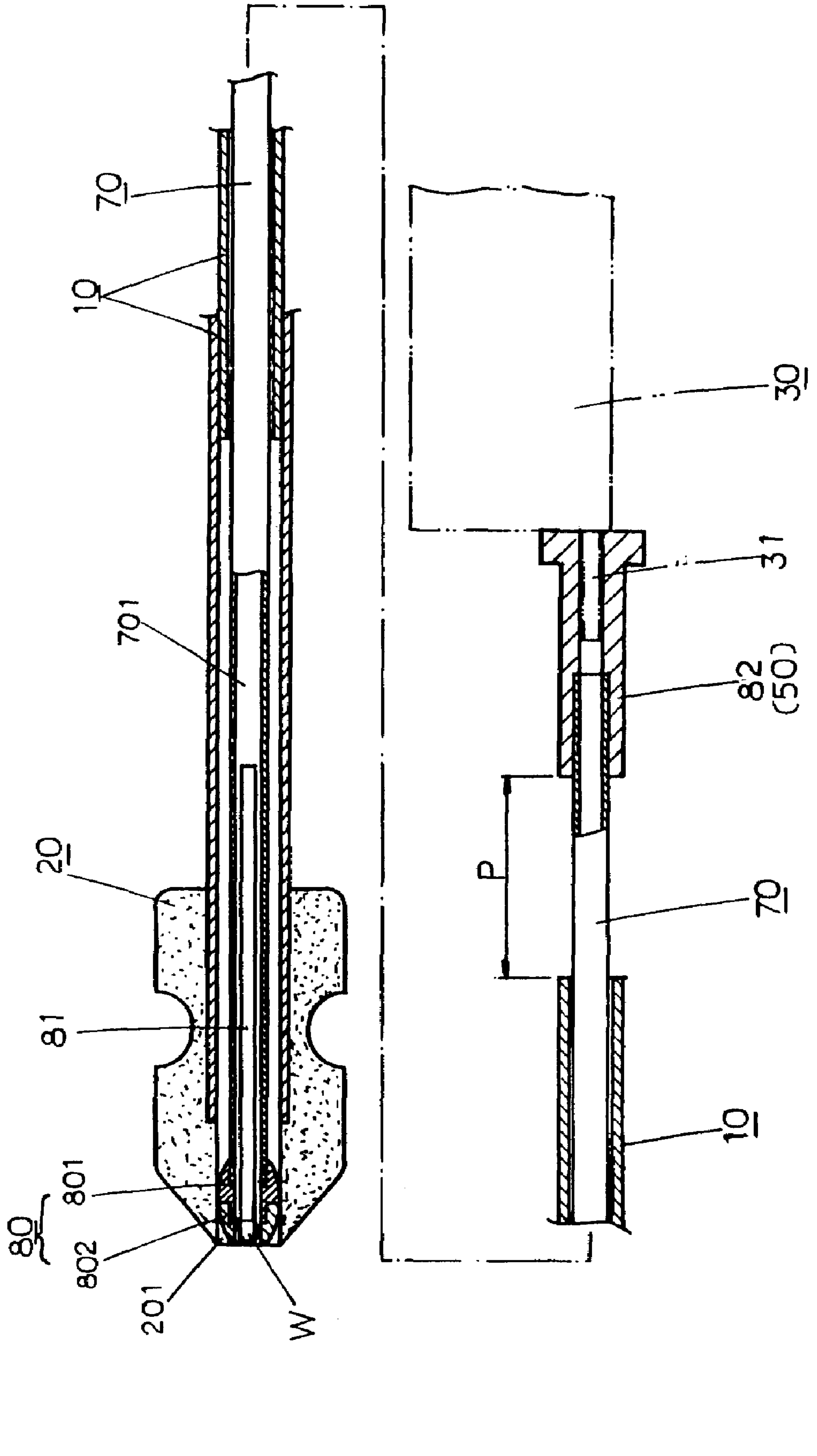
FIG. 8 is a schematic view of the present invention.
Figure 9:
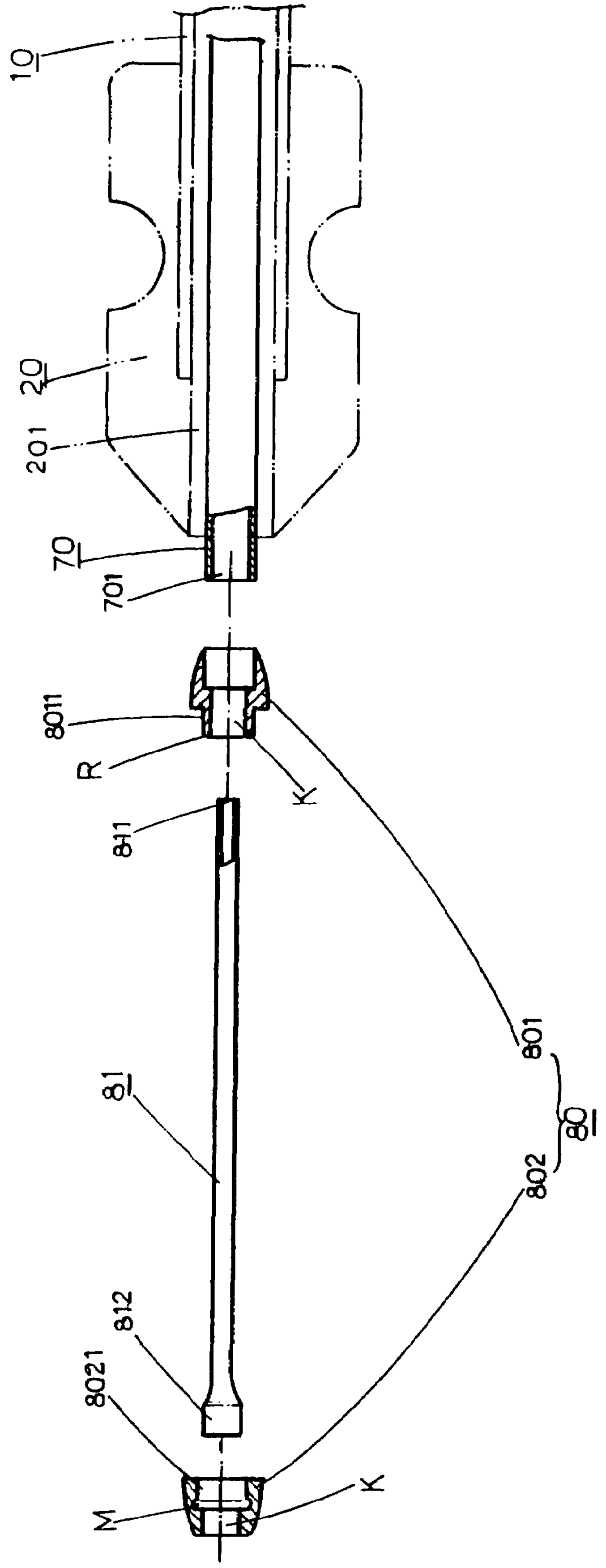
FIG. 9 is an exploded view of the invention in FIG. 8.
Figure 10:
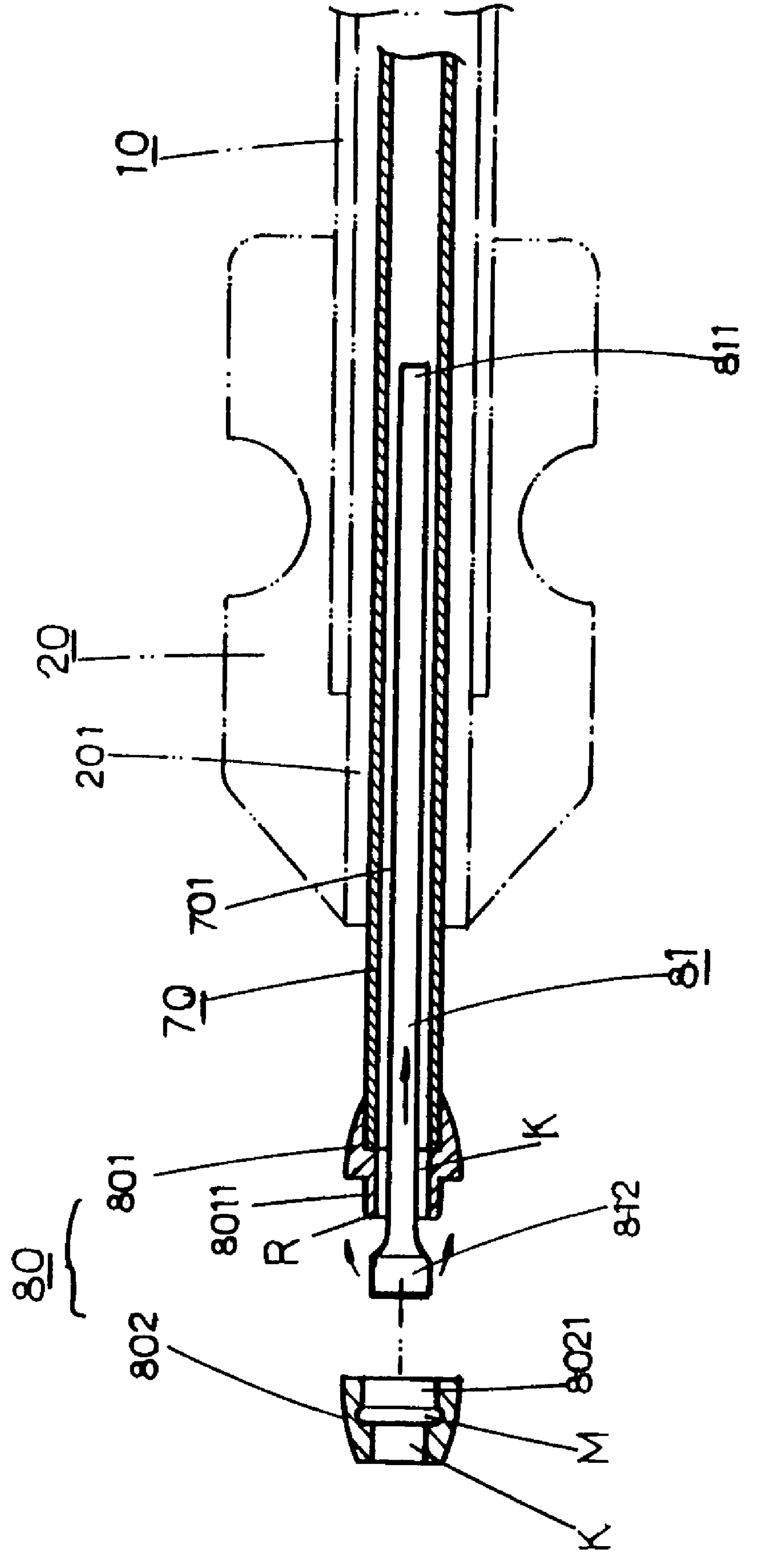
FIG. 10 is a schematic view of first sheath body of the second nozzle shown in FIG. 9 coupled to the front end of inner catheter.
Figure 11:
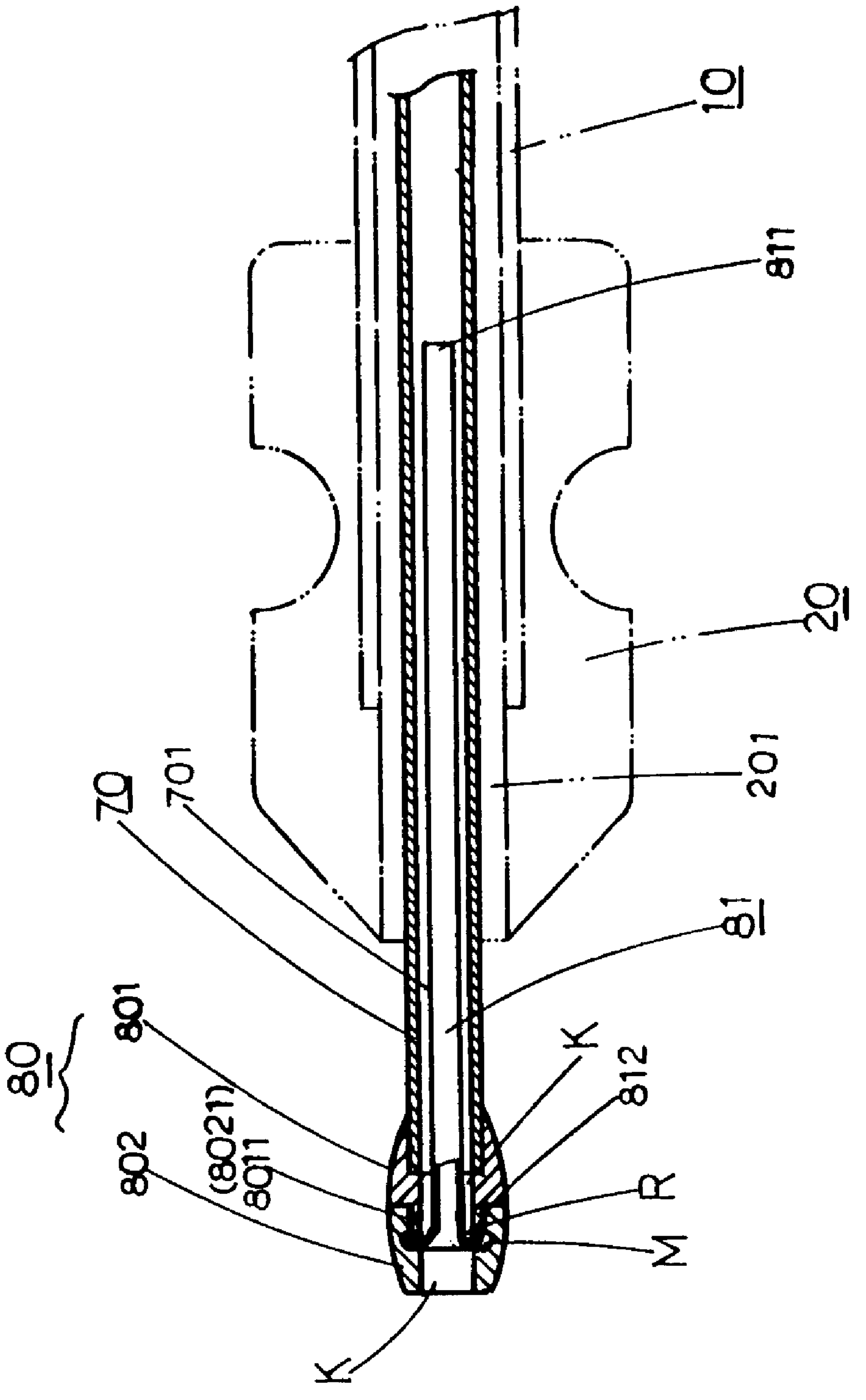
FIG. 11 is a schematic view of the second nozzle and thin flexible tube as shown in FIG. 9 mounted at the front end of inner catheter.
Figure 12:
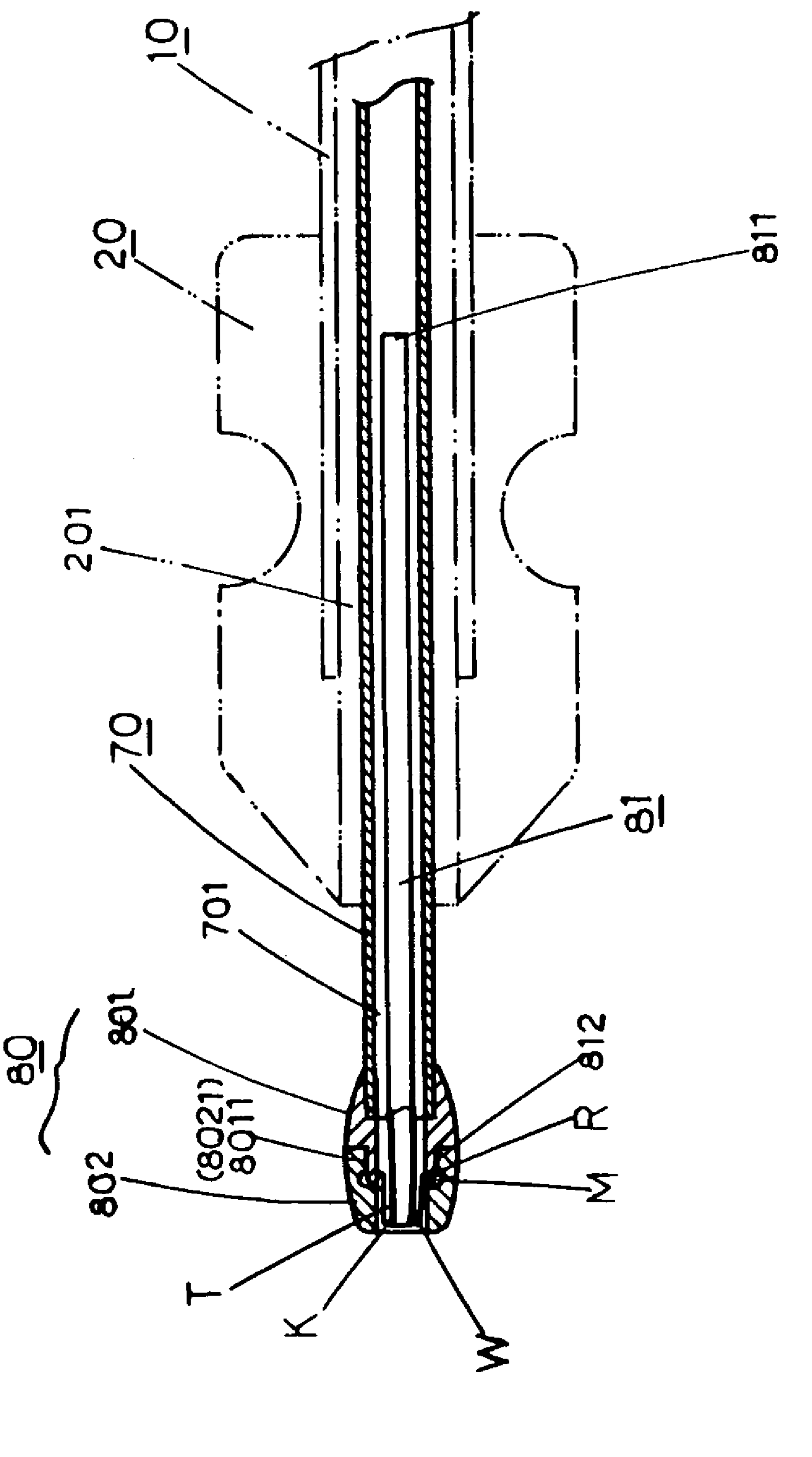
FIG. 12 is a schematic view showing an outward unfolding guide member disposed at the rear end of thin flexible tube according to the invention.
Figure 13:
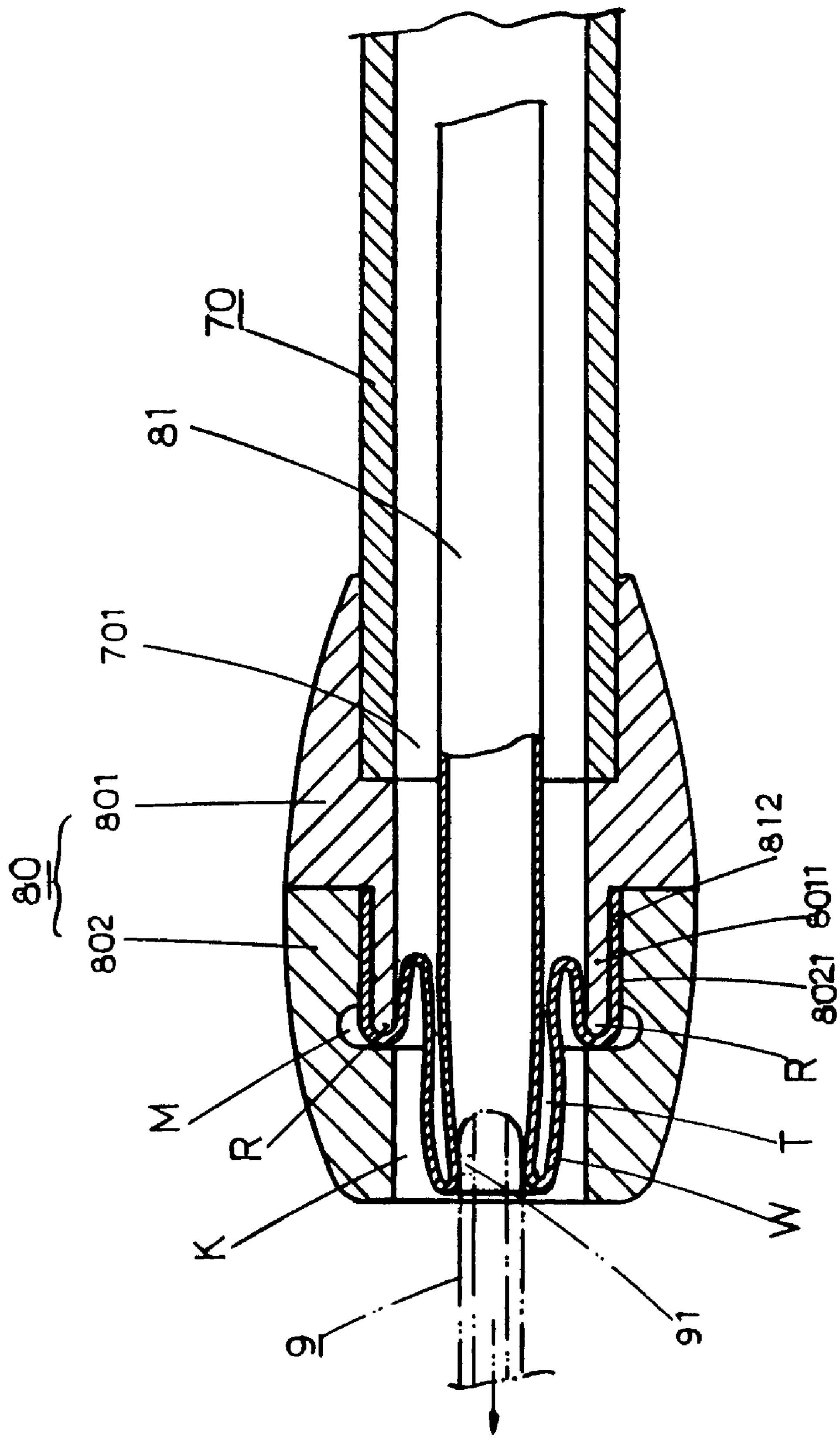
FIG. 13 is a magnified view showing part of FIG. 12.

As show in FIG. 8, the improved artificial insemination device with an inner catheter for animals according to the invention features an inner catheter movably disposed inside a catheter tube 10 of the artificial insemination device with a thin flexible tube 81 and a positioning stop member 82 configured at its front and rear ends respectively. Also referring to FIGS. 9, 10, 11, 12, and 13, the thin flexible tube 81 is mounted at the front end of inner catheter through a second nozzle 80; the second nozzle is an assembly of a first sheath body 801 and a second sheath body 802 made of material with proper rigidity and elasticity. That is, one end of the first sheath body 801 is securely mounted to the front end of inner catheter 70, while its other end is arranged with an insertion member 8011 of smaller diameter. The outer end of insertion member 8011 is provided with a chamfer R, while its center is disposed with a through guide hole K; the diameter of the thin flexible tube 81 is smaller than the lumen 701 of inner catheter 70 where its open front end 811 is inserted inversely into inner catheter 70 through the guide hole K of first sheath body 801 and extends inwardly to the lumen 701 of inner catheter 70, while its rear end inversely envelops the insertion member 8011 of first sheath body 801. The second sheath body 802 is provided with a sheathing member 8021 that engages exactly the insertion member 8011 of first sheath body 802; its inner end is disposed with an enlarging slot member M and its center is arranged with a through guide hole K. When sheathing member 8021 is assembled to the insertion member 8011 of first sheath body 801, the guide hole K of second sheath body 802 secures the rear end 812 of the thin flexible tube 81 exactly and the slot member M at the inner end corresponds exactly to the chamfer R at outer end of insertion member 8011 without contacting each other (FIG. 13), such that the rear end of thin flexible tube 81 that envelops the chamber R of insertion member will not perforate due to friction.

The inner catheter 70 may be mounted inside the catheter tube 10 and nozzle 20 in advance as in prior art and then have the second nozzle 80 and the thin flexible tube 81 disposed at its front end, or the inner catheter 70 may have the second nozzle 80 and the thin flexible tube 81 disposed at its front end and then have its rear end inserted into the catheter tube 10 from nozzle 20. After the second nozzle 80 is mounted at the front end of inner catheter 70, it may be exposed at the front of nozzle 20 or concealed inside the center hole 201 of nozzle 20.

After the second nozzle and thin flexible tube 81 are positioned at the front end of inner catheter 70, and the inner catheter 70 is inserted into catheter tube 10 with the front of second nozzle 80 aligning with the front of nozzle 20 (as shown in FIG. 8) or the rear of second nozzle 80 aligning with the front of nozzle 20, the positioning stop member 82 is directly mounted on the exposed portion of inner catheter 70 at P distance apart from the rear end of catheter tube 10. As such, the distance inner catheter 70 can advance is based on the set distance of P. The positioning stop member 82 may be a clipping fastening, or sheathing means so long as it can be securely mounted on inner catheter 70 (the example cited below is a connector 50 for the insertion of insertion tube 31 of semen bottle, bag or syringe 30).

Again referring to FIG. 12 and FIG. 13, after the thin flexible tube 81 is disposed at the front end of inner catheter 70 via the second nozzle 80, the rear end of thin flexible tube 81 at the guide hole K of second nozzle 80 and having a guide member W that unfolds in an inside-out manner forms an accommodation space T. The accommodation space T communicates directly with the lumen 701 of inner catheter 70, while the guide member W is positioned exactly at where guide hole K of the second sheath body 802 of the second nozzle 80 is located. There are a number of means to enable the guide member W to unfold inside out. For example, insert an air rod 9 through the second nozzle 80 and position it behind the thin flexible tube 81; next adjoin the air hole 91 at the front of air rod 9 to the inner circumference of thin flexible tube 81 and begin air extraction to suck the portion of inner circumference of thin flexible tube 81 that corresponds to the air hole 91; pull out air rod 9 gradually to form an outward unfolding guide member W on the thin flexible tube 81. This way, guide member W is formed in an easy, convenient and swift manner.

Figure 14:
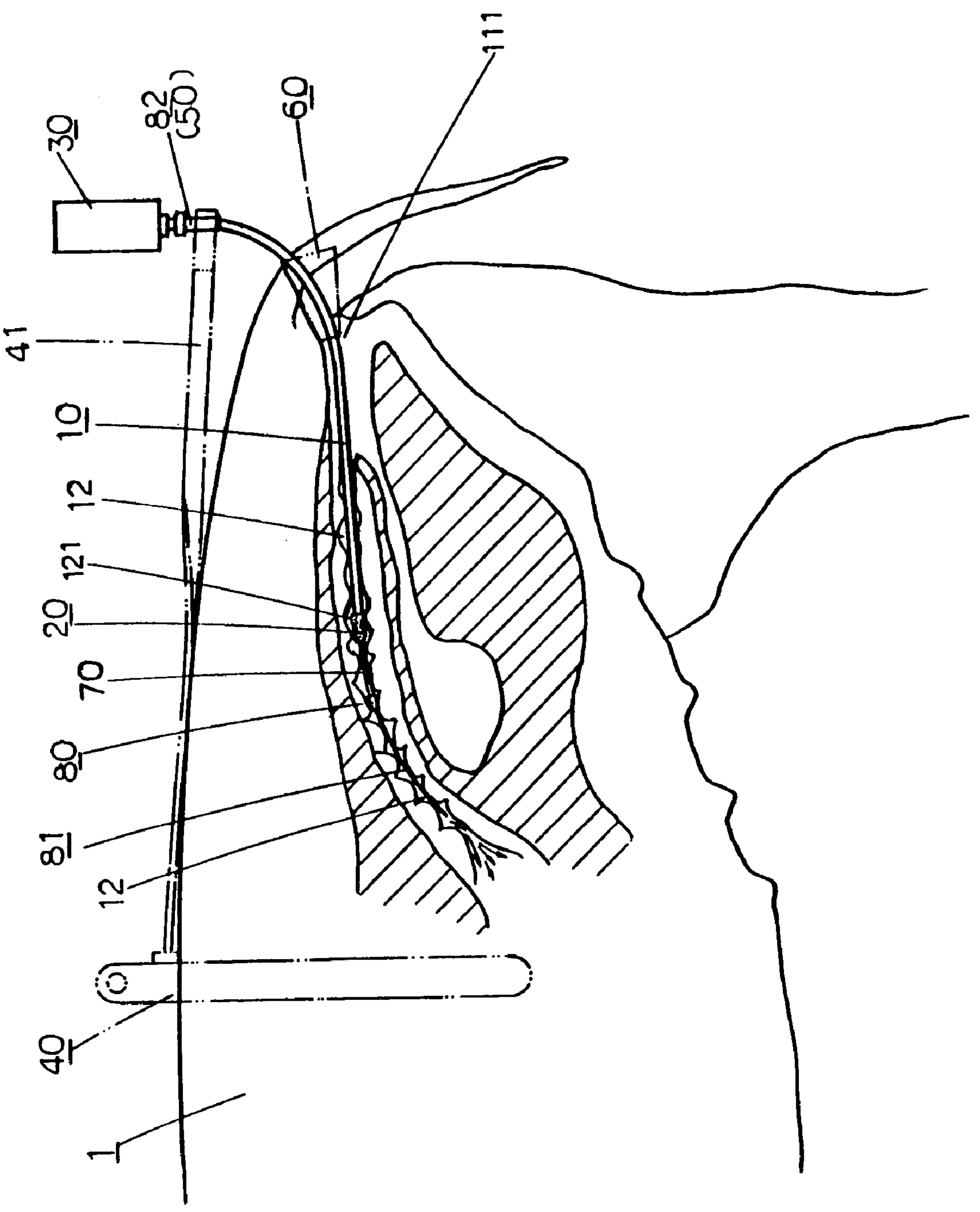
FIG. 14 shows the deployment of the invention in the body of a female animal.
Figure 15:
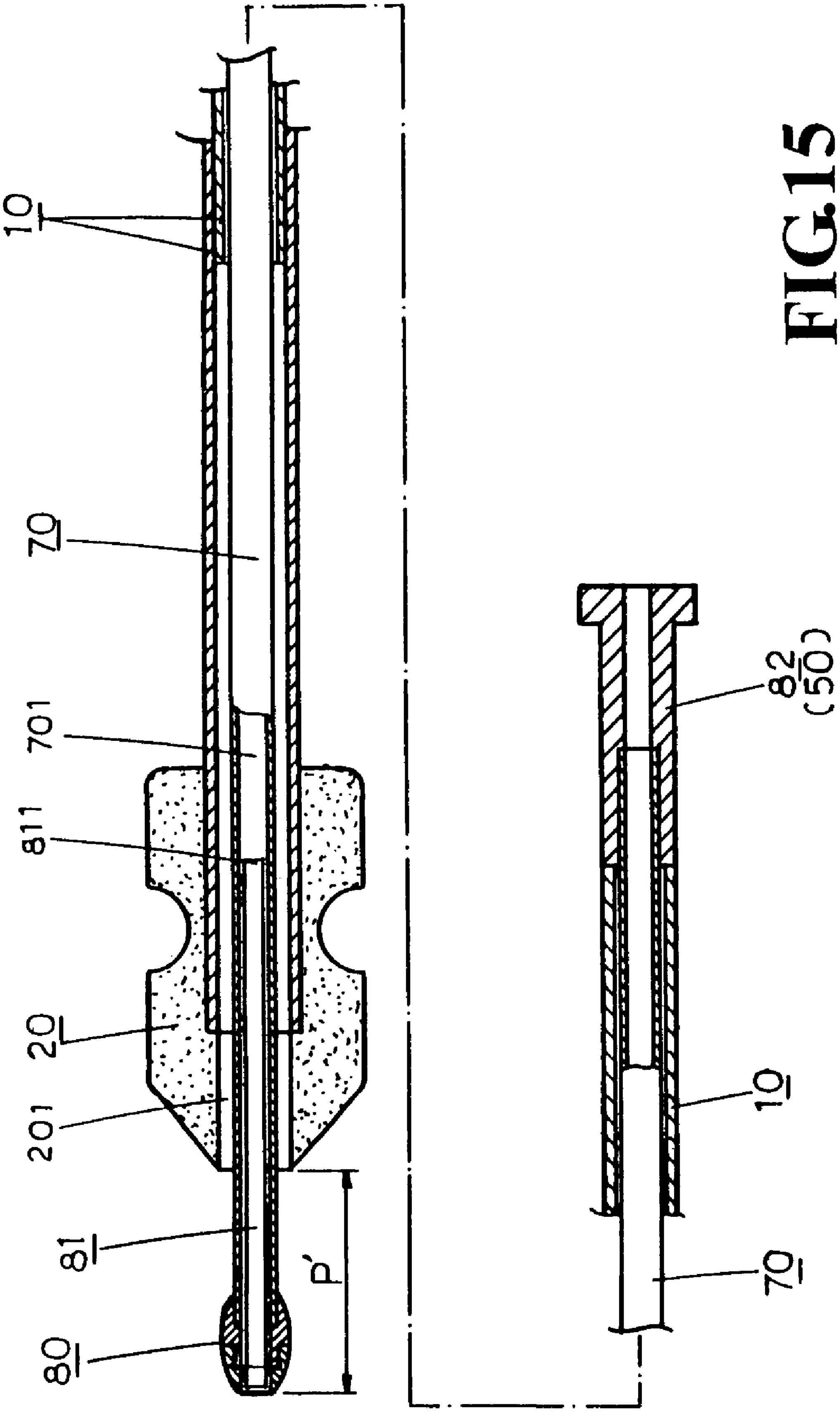
FIG. 15 shows the inner catheter and the second nozzle of the invention in the state of outward extension.
Figure 16:
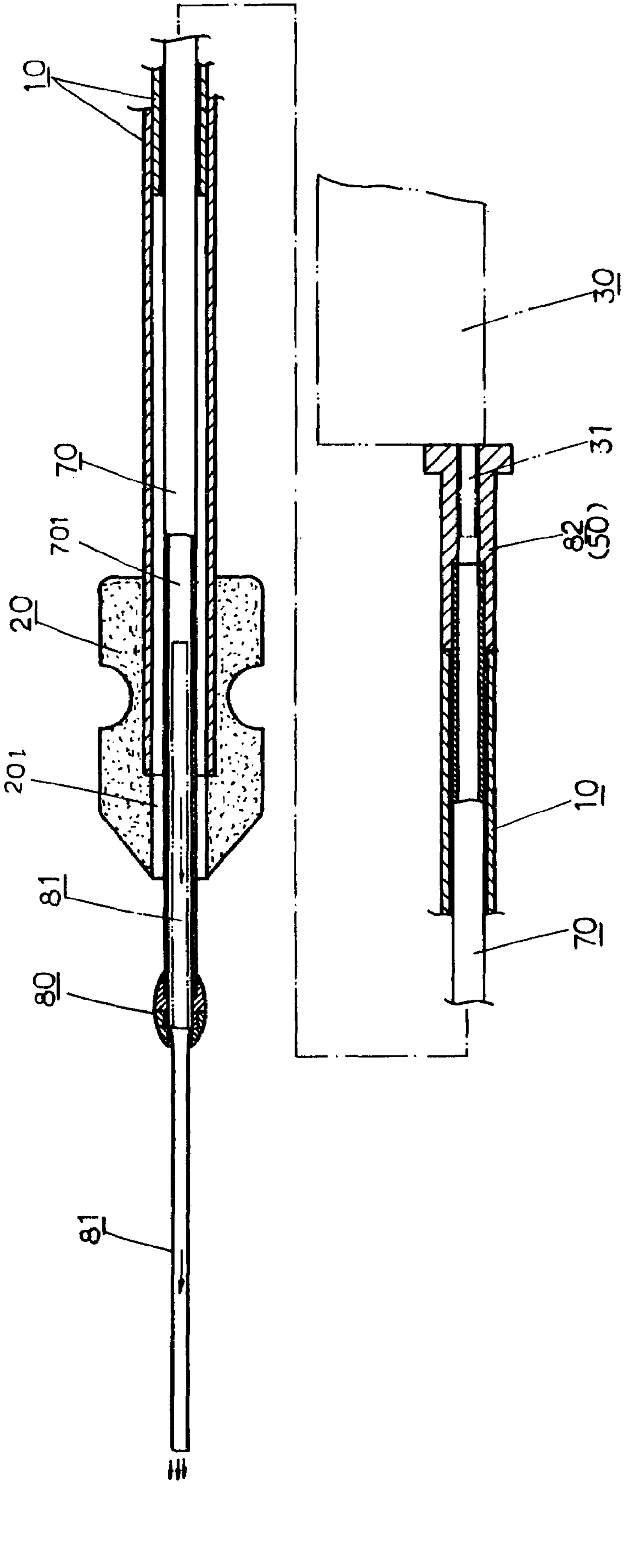
FIG. 16 shows the thin flexible tube of the invention in the state of outward extension.

Referring to FIGS. 14, 15, and 16, the operator would use conventional operating procedure when using the present invention for artificial insemination in animals. That is, the nozzle 20 and catheter tube 10 are inserted into the vagina 11 of animal body 1 through guide bush 60, where nozzle 20 is extended approximately to the position of first cervical ring 121 of cervical tract 12. Next, the inner catheter 70 is pushed inward so that it and the second nozzle 80 at its front end extend into cervical tract 12 from nozzle 20; when the inner catheter 70 is pushed inward, it would advance no more than a set distance of P because of the positioning stop member 82 provided at its rear end and the set space of P between the positioning stop member 82 and the rear end of catheter tube 10 (FIG. 8). As such, the second nozzle 80 is exposed outside nozzle 20 at an equidistance of P' and will not reach too far into the uterus of animal as in prior art to traumatize the uterus. After the inner catheter 70 is pushed inward, the catheter tube 10 and the positioning stop member 82 may be bent upward and secured to the positioning strap 41 of AI Buddy 40 as in prior art, or left unbent and laid directly outside the vaginal orifice 111 of female animal 1. The insertion tube 31 of semen dispenser (bag or syringe) 30 is then inserted into the rear end of inner catheter 70 or connector 50 (connector 50 is used as a positioning stop member 82 in this example) and semen fluid is squeezed in.

Because the front end of thin flexible tube 81 is inversely inserted into the front end of inner catheter 70, the second nozzle 80 at the front end of inner catheter 70 is in somewhat closed state. When semen is squeezed into the lumen 701 from the rear end of inner catheter 70, the inversely inserted thin flexible tube 81 is also under the exertion of pressure and automatically pushes forward. In particular, because the outwardly unfolding guide member W provided at the rear end of thin flexible tube 81 around the guide hole K of second nozzle 80 forms an accommodation space T that communicates with the lumen 701 of inner catheter (FIG. 12 and FIG. 13), semen squeezed into the lumen 701 of inner catheter will directly fill the accommodation space T and exert pressure. Naturally, the entire thin flexible tube 81 would gradually unfold outwardly from its guide member W and extend forward, and deposit semen into the uterus after it is totally extended. That is, because the thin flexible tube 81 is smaller than the lumen 701 of inner catheter and has a certain length, it advances fast along the cervical tract with practically no friction when it extends gradually from the second nozzle 80 under the pressure of semen. When the thin flexible tube 81 is completely stretched, its open front end 811 will reach the uterus or its vicinity to deposit semen into the uterus, thereby completing the artificial insemination procedure in a highly efficient manner.

As described above, the thin flexible tube 81 is smaller than the lumen 701 of inner catheter, made of pliable material and is of certain length, and its front end 811 is open when semen is deposited into inner catheter 70. But the semen in the inner catheter 70 will not flow out from the open front end 811, but instead, squeezes and closes the front end 811, and is automatically expelled from the front end 811 when the entire thin flexible tube 81 becomes extended. Also because of the pliable nature of thin flexible tube 81, it will advance in the cervical tract 12 smoothly and swiftly without traumatizing the delicate tissue of cervical tract 12 or the uterus.

Because the outwardly unfolding guide member W provided on the thin flexible tube 81 of inner catheter forms an accommodation space T that communicates with an inner catheter 70, semen squeezed into the inner catheter 70 will directly fill the accommodation space T and exert pressure, which pushes the entire thin flexible tube 81 to unfold inside-out quickly and smoothly. As such, minimal squeeze force is required, which renders the whole operation convenient and simple.

Because the inner catheter 70 has smaller diameter than catheter tube 10 and the thin flexible tube 81 therein is even smaller than its lumen 701, the thin flexible tube 81 is able to deliver semen swiftly to uterus after its is fully extended. As such, semen used for artificial insemination does not require massive dilution, while only more concentrated semen in small amount needs to be injected into the inner catheter. Thus the present invention not only offers the economic benefit of saving the semen used, the fertilization rate and the number of fetus are also expected to increase.

As described above, the second nozzle 80 is smaller than nozzle 20 and may be directly extended into the cervical tract 12 of animal. But because the second nozzle 80 is made of rubber material with proper rigidity and elasticity, there is no concern of it traumatizing cervical tract 12 when it advances in it. More so, confined by the advancing length P of inner catheter 70, second nozzle 80 is not expected to reach into uterus and traumatize it. In addition, because the second nozzle 80 has proper rigidity and elasticity, it will not deform to block the extension of thin flexible tube 71 when it is pushed into cervical tract by inner catheter 70, but instead, enables the thin flexible tube 811 to deliver the semen to the uterus to complete the insemination process in an efficient manner.

What is claimed is:

1. An improved artificial insemination device with an inner catheter for animals, having a catheter tube, a first nozzle, an inner catheter, a second nozzle and a connector; the nozzle being assembled at the front end of the catheter tube, the inner catheter being movably installed inside the catheter tube, the second nozzle being assembled at the front end of the inner catheter, and the connector being installed posterior to the catheter tube for the insertion of an insertion tube of semen dispenser, said semen dispenser being a bag or syringe comprising;

a positioning stop member being mounted at the rear end of the inner catheter that allows the second nozzle to be exposed outside the first nozzle for a length equivalent to the set distance between the positioning stop member and the rear end of catheter tube when the inner catheter is pushed inward;

a thin flexible tube made in smaller diameter than the lumen of inner catheter has its rear end secured to the second nozzle and its open front end inversely inserted into the lumen of the inner catheter;

when the rear end of the inner catheter is pushed inward, the positioning stop member thereon moves a set distance and checks the rear end of the catheter tube, while the second nozzle extends outside the nozzle for a length based on the distance the inner catheter is advanced and reaches the cervical tract of an animal; when semen is squeezed in from the rear end of the inner catheter, the thin flexible tube unfolds outward gradually from a guide hole of the second nozzle, extends to uterus or its vicinity along the cervical tract, and deposits the semen into the uterus.

2. An improved artificial insemination device with an inner catheter for animals as claimed in claim 1, wherein the positioning stop member mounted at the rear end of inner catheter is a clipping, fastening or sheathing means.

3. An improved artificial insemination device with an inner catheter for animals as claimed in claim 1, wherein the second nozzle is an assembly of a first sheath body and a second sheath body made of rubber material and having proper rigidity and elasticity; one end of the first sheath body is secured to the front end of inner catheter, its other end is disposed with an insertion member of smaller diameter for inverse wrapping by the rear end of thin flexible tube, and its center is provided with a though guide hole; the second sheath body is configured with a sheathing member that engages exactly the insertion member of first sheath body and secures the rear end of thin flexible tube upon engagement; and its center is arranged with a through guide hole.

4. An improved artificial insemination device with an inner catheter for animals as claimed claim 1, wherein after the thin flexible tube is mounted at the front end of the inner catheter via the second nozzle, its rear end situated at the guide hole of second nozzle is provided with a guide member that unfolds inside-out to form an accommodation space which communicates with the lumen of inner catheter.

5. An improved artificial insemination device with an inner catheter for animals as claimed in claim 1, wherein the outer end of insertion member of the first sheath body of second nozzle is provided with a chamfer, while the inner end of the sheathing member of second sheath body is disposed with an enlarging slot member; the chamfer and the slot member oppose each other without contact when the insertion member of first sheath body engages the sheathing member of second sheath body.

* * * * *